United States Patent
Farascioni (10) Patent No.: US 7,896,214 B2
(45) Date of Patent: Mar. 1, 2011

(54) TISSUE STOP FOR SURGICAL INSTRUMENT

(75) Inventor: David Farascioni, Bethel, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 133 days.

(21) Appl. No.: 12/235,751

(22) Filed: Sep. 23, 2008

(65) Prior Publication Data

US 2010/0072257 A1   Mar. 25, 2010

(51) Int. Cl.
*A61B 17/068* (2006.01)
(52) U.S. Cl. .................. 227/180.1; 227/19; 227/175.1; 227/179.1
(58) Field of Classification Search ............. 227/180.1, 227/175.1, 19, 179.1
See application file for complete search history.

(56) References Cited

U.S. PATENT DOCUMENTS

| | | | |
|---|---|---|---|
| 3,017,637 A | 1/1962 | Sampson | |
| 3,079,606 A | 3/1963 | Bobrov et al. | |
| 3,490,675 A | 1/1970 | Green et al. | |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,244,372 A | 1/1981 | Kapitanov et al. | |
| 4,429,695 A | 2/1984 | Green | |
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |

(Continued)

FOREIGN PATENT DOCUMENTS

AU        5476586        9/1986

(Continued)

OTHER PUBLICATIONS

European Search Report for EP 09252249.9-1269 date of completion is Nov. 18, 2009 (3 pages).

*Primary Examiner*—Brian D Nash (57) ABSTRACT

A surgical including a handle assembly, an elongated portion, an end effector, and a stop member is disclosed. The elongated portion extends distally from the handle assembly. The end effector is disposed adjacent a distal portion of the elongated portion and includes a first jaw member and a second jaw member. At least one jaw member is movable with respect to the other jaw member between spaced and approximated positions. The stop member is disposed adjacent a distal portion of the first jaw member and is pivotable with respect to the first jaw member between a first position, a significant portion of the stop member being positioned external to the first jaw member, and a second position capturing the tissue between the first jaw member and second jaw member.

8 Claims, 10 Drawing Sheets

U.S. PATENT DOCUMENTS

| | | |
|---|---|---|
| 4,784,137 A | 11/1988 | Kulik et al. |
| 4,863,088 A | 9/1989 | Redmond et al. |
| 4,869,415 A | 9/1989 | Fox |
| 4,881,544 A | 11/1989 | Green et al. |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,008 A | 11/1995 | Rodak |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |

| | | | | | |
|---|---|---|---|---|---|
| 5,626,587 A | 5/1997 | Bishop et al. | 5,820,009 A | 10/1998 | Melling et al. |
| 5,628,446 A | 5/1997 | Geiste et al. | 5,823,066 A | 10/1998 | Huitema et al. |
| 5,630,539 A | 5/1997 | Plyley et al. | 5,826,776 A | 10/1998 | Schulze et al. |
| 5,630,540 A | 5/1997 | Blewett | 5,829,662 A | 11/1998 | Allen et al. |
| 5,630,541 A | 5/1997 | Williamson, IV et al. | 5,833,695 A | 11/1998 | Yoon |
| 5,632,432 A | 5/1997 | Schulze et al. | 5,836,147 A | 11/1998 | Schnipke |
| 5,634,584 A | 6/1997 | Okorocha et al. | 5,862,972 A | 1/1999 | Green et al. |
| 5,636,780 A | 6/1997 | Green et al. | 5,865,361 A | 2/1999 | Milliman et al. |
| 5,645,209 A | 7/1997 | Green et al. | 5,871,135 A | 2/1999 | Williamson, IV et al. |
| 5,647,526 A | 7/1997 | Green et al. | 5,873,873 A | 2/1999 | Smith et al. |
| 5,651,491 A | 7/1997 | Heaton et al. | 5,878,938 A | 3/1999 | Bittner et al. |
| 5,653,373 A | 8/1997 | Green et al. | 5,893,506 A | 4/1999 | Powell |
| 5,653,374 A | 8/1997 | Young et al. | 5,894,979 A | 4/1999 | Powell |
| 5,653,721 A | 8/1997 | Knodel et al. | 5,897,562 A | 4/1999 | Bolanos et al. |
| 5,655,698 A | 8/1997 | Yoon | 5,901,895 A | 5/1999 | Heaton et al. |
| 5,657,921 A | 8/1997 | Young et al. | 5,911,352 A | 6/1999 | Racenet et al. |
| 5,658,300 A | 8/1997 | Bito et al. | 5,911,353 A | 6/1999 | Bolanos et al. |
| 5,662,258 A | 9/1997 | Knodel et al. | 5,918,791 A | 7/1999 | Sorrentino et al. |
| 5,662,259 A | 9/1997 | Yoon | 5,919,198 A | 7/1999 | Graves, Jr. et al. |
| 5,662,260 A | 9/1997 | Yoon | 5,922,001 A | 7/1999 | Yoon |
| 5,662,662 A | 9/1997 | Bishop et al. | 5,931,847 A | 8/1999 | Bittner et al. |
| 5,662,666 A | 9/1997 | Onuki et al. | 5,941,442 A | 8/1999 | Geiste et al. |
| 5,665,085 A | 9/1997 | Nardella | 5,954,259 A | 9/1999 | Viola et al. |
| 5,667,517 A | 9/1997 | Hooven | 5,980,510 A | 11/1999 | Tsonton et al. |
| 5,669,544 A | 9/1997 | Schulze et al. | 5,988,479 A | 11/1999 | Palmer |
| 5,673,840 A | 10/1997 | Schulze et al. | 6,004,335 A | 12/1999 | Vaitekunas et al. |
| 5,673,841 A | 10/1997 | Schulze et al. | 6,010,054 A | 1/2000 | Johnson et al. |
| 5,673,842 A | 10/1997 | Bittner et al. | 6,032,849 A | 3/2000 | Mastri et al. |
| 5,676,674 A | 10/1997 | Bolanos et al. | 6,045,560 A | 4/2000 | McKean et al. |
| 5,680,981 A | 10/1997 | Mililli et al. | 6,063,097 A | 5/2000 | Oi et al. |
| 5,680,982 A | 10/1997 | Schulze et al. | 6,079,606 A | 6/2000 | Milliman et al. |
| 5,690,269 A | 11/1997 | Bolanos et al. | 6,099,551 A | 8/2000 | Gabbay |
| 5,692,668 A | 12/1997 | Schulze et al. | 6,109,500 A | 8/2000 | Alli et al. |
| 5,697,542 A | 12/1997 | Knodel et al. | 6,131,789 A | 10/2000 | Schulze et al. |
| 5,702,409 A | 12/1997 | Rayburn et al. | 6,131,790 A | 10/2000 | Piraka |
| 5,704,534 A | 1/1998 | Huitema et al. | 6,155,473 A | 12/2000 | Tompkins et al. |
| 5,706,997 A | 1/1998 | Green et al. | 6,197,017 B1 | 3/2001 | Brock et al. |
| 5,709,334 A | 1/1998 | Sorrentino et al. | 6,202,914 B1 | 3/2001 | Geiste et al. |
| 5,711,472 A | 1/1998 | Bryan | 6,241,139 B1 | 6/2001 | Milliman et al. |
| 5,713,505 A | 2/1998 | Huitema | 6,250,532 B1 | 6/2001 | Green et al. |
| 5,715,988 A | 2/1998 | Palmer | 6,264,086 B1 | 7/2001 | McGuckin, Jr. |
| 5,716,366 A | 2/1998 | Yates | 6,264,087 B1 | 7/2001 | Whitman |
| 5,718,359 A | 2/1998 | Palmer et al. | 6,269,977 B1 | 8/2001 | Moore |
| 5,725,536 A | 3/1998 | Oberlin et al. | 6,279,809 B1 | 8/2001 | Nicolo |
| 5,725,554 A | 3/1998 | Simon et al. | 6,315,183 B1 | 11/2001 | Piraka |
| 5,728,110 A | 3/1998 | Vidal et al. | 6,315,184 B1 | 11/2001 | Whitman |
| 5,732,806 A | 3/1998 | Foshee et al. | 6,325,810 B1 | 12/2001 | Hamilton et al. |
| 5,735,848 A | 4/1998 | Yates et al. | 6,330,965 B1 | 12/2001 | Milliman et al. |
| 5,743,456 A | 4/1998 | Jones et al. | 6,391,038 B2 | 5/2002 | Vargas et al. |
| 5,749,893 A | 5/1998 | Vidal et al. | 6,398,797 B2 | 6/2002 | Bombard et al. |
| 5,752,644 A | 5/1998 | Bolanos et al. | 6,436,097 B1 | 8/2002 | Nardella |
| 5,762,255 A | 6/1998 | Chrisman et al. | 6,439,446 B1 | 8/2002 | Perry et al. |
| 5,762,256 A | 6/1998 | Mastri et al. | 6,443,973 B1 | 9/2002 | Whitman |
| 5,769,303 A | 6/1998 | Knodel et al. | 6,463,623 B2 | 10/2002 | Ahn et al. |
| 5,769,892 A | 6/1998 | Kingwell | 6,478,804 B2 | 11/2002 | Vargas et al. |
| 5,772,099 A | 6/1998 | Gravener | 6,488,196 B1 | 12/2002 | Fenton, Jr. |
| 5,772,673 A | 6/1998 | Cuny et al. | 6,503,257 B2 | 1/2003 | Grant et al. |
| 5,779,130 A | 7/1998 | Alesi et al. | 6,505,768 B2 | 1/2003 | Whitman |
| 5,779,131 A | 7/1998 | Knodel et al. | 6,544,274 B2 | 4/2003 | Danitz et al. |
| 5,779,132 A | 7/1998 | Knodel et al. | 6,554,844 B2 | 4/2003 | Lee et al. |
| 5,782,396 A | 7/1998 | Mastri et al. | 6,565,554 B1 | 5/2003 | Niemeyer |
| 5,782,397 A | 7/1998 | Koukline | 6,587,750 B2 | 7/2003 | Gerbi et al. |
| 5,782,834 A | 7/1998 | Lucey et al. | 6,592,597 B2 | 7/2003 | Grant et al. |
| 5,785,232 A | 7/1998 | Vidal et al. | 6,594,552 B1 | 7/2003 | Nowlin et al. |
| 5,797,536 A | 8/1998 | Smith et al. | 6,602,252 B2 | 8/2003 | Mollenauer |
| 5,797,537 A | 8/1998 | Oberlin et al. | 6,612,053 B2 | 9/2003 | Liao |
| 5,797,538 A | 8/1998 | Heaton et al. | 6,619,529 B2 | 9/2003 | Green et al. |
| 5,810,811 A | 9/1998 | Yates et al. | 6,644,532 B2 | 11/2003 | Green et al. |
| 5,810,855 A | 9/1998 | Rayburn et al. | 6,656,193 B2 | 12/2003 | Grant et al. |
| 5,814,055 A | 9/1998 | Knodel et al. | 6,669,073 B2 | 12/2003 | Milliman et al. |
| 5,814,057 A | 9/1998 | Oi et al. | 6,681,978 B2 | 1/2004 | Geiste et al. |
| 5,816,471 A | 10/1998 | Plyley et al. | 6,698,643 B2 | 3/2004 | Whitman |
| 5,817,109 A | 10/1998 | McGarry et al. | 6,716,232 B1 | 4/2004 | Vidal et al. |

| | | | | | | |
|---|---|---|---|---|---|---|
| 6,722,552 | B2 | 4/2004 | Fenton, Jr. | 7,367,485 B2 | 5/2008 | Shelton, IV et al. |
| 6,731,473 | B2 | 5/2004 | Li et al. | 7,380,695 B2 | 6/2008 | Doll et al. |
| 6,755,338 | B2 | 6/2004 | Hahnen et al. | 7,380,696 B2 | 6/2008 | Shelton, IV et al. |
| 6,783,524 | B2 | 8/2004 | Anderson et al. | 7,399,310 B2 | 7/2008 | Edoga et al. |
| 6,786,382 | B1 | 9/2004 | Hoffman | 7,401,720 B1 | 7/2008 | Durrani |
| 6,808,262 | B2 | 10/2004 | Chapoy et al. | 7,404,508 B2 | 7/2008 | Smith et al. |
| 6,817,509 | B2 | 11/2004 | Geiste et al. | 7,404,509 B2 | 7/2008 | Ortiz et al. |
| 6,830,174 | B2 | 12/2004 | Hillstead et al. | 7,407,074 B2 | 8/2008 | Ortiz et al. |
| 6,835,199 | B2 | 12/2004 | McGuckin, Jr. et al. | 7,407,077 B2 | 8/2008 | Ortiz et al. |
| 6,843,403 | B2 | 1/2005 | Whitman | 7,407,078 B2 | 8/2008 | Shelton, IV et al. |
| RE38,708 | E | 3/2005 | Bolanos et al. | 7,416,101 B2 | 8/2008 | Shelton, IV et al. |
| 6,877,647 | B2 | 4/2005 | Green et al. | 7,419,080 B2 | 9/2008 | Smith et al. |
| 6,879,880 | B2 | 4/2005 | Nowlin et al. | 7,419,495 B2 | 9/2008 | Menn et al. |
| 6,889,116 | B2 | 5/2005 | Jinno | 7,422,139 B2 | 9/2008 | Shelton, IV et al. |
| 6,905,057 | B2 | 6/2005 | Swayze et al. | 7,431,189 B2 | 10/2008 | Shelton, IV et al. |
| 6,953,138 | B1 | 10/2005 | Dworak et al. | 7,434,715 B2 | 10/2008 | Shelton, IV et al. |
| 6,953,139 | B2 | 10/2005 | Milliman et al. | 7,434,717 B2 | 10/2008 | Shelton, IV et al. |
| 6,959,852 | B2 | 11/2005 | Shelton, IV et al. | 7,438,208 B2 | 10/2008 | Larson |
| 6,962,594 | B1 | 11/2005 | Thevenet | 7,438,209 B1 | 10/2008 | Hess et al. |
| 6,964,363 | B2 | 11/2005 | Wales et al. | 7,441,684 B2 | 10/2008 | Shelton, IV et al. |
| 6,978,921 | B2 | 12/2005 | Shelton, IV et al. | 7,448,525 B2 | 11/2008 | Shelton, IV et al. |
| 6,981,628 | B2 | 1/2006 | Wales | 7,451,904 B2 | 11/2008 | Shelton, IV |
| 6,986,451 | B1 | 1/2006 | Mastri et al. | 7,455,208 B2 | 11/2008 | Wales et al. |
| 6,988,649 | B2 | 1/2006 | Shelton, IV et al. | 7,458,494 B2 | 12/2008 | Matsutani et al. |
| 6,991,627 | B2 | 1/2006 | Madhani et al. | 7,462,185 B1 | 12/2008 | Knodel |
| 6,994,714 | B2 | 2/2006 | Vargas et al. | 7,464,846 B2 | 12/2008 | Shelton, IV et al. |
| 7,000,818 | B2 | 2/2006 | Shelton, IV et al. | 7,464,849 B2 | 12/2008 | Shelton, IV et al. |
| 7,000,819 | B2 | 2/2006 | Swayze et al. | 7,467,740 B2 | 12/2008 | Shelton, IV et al. |
| 7,032,799 | B2 | 4/2006 | Viola et al. | 7,472,815 B2 | 1/2009 | Shelton, IV et al. |
| 7,044,352 | B2 | 5/2006 | Shelton, IV et al. | 7,473,258 B2 | 1/2009 | Clauson et al. |
| 7,044,353 | B2 | 5/2006 | Mastri et al. | 2002/0004498 A1 | 1/2002 | Doherty |
| 7,055,730 | B2 | 6/2006 | Ehrenfels et al. | 2002/0009193 A1 | 1/2002 | Deguchi |
| 7,055,731 | B2 | 6/2006 | Shelton, IV et al. | 2002/0018323 A1 | 2/2002 | Li |
| 7,059,508 | B2 | 6/2006 | Shelton, IV et al. | 2002/0032948 A1 | 3/2002 | Ahn |
| 7,070,083 | B2 | 7/2006 | Jankowski | 2002/0036748 A1 | 3/2002 | Chapoy |
| 7,083,075 | B2 | 8/2006 | Swayze et al. | 2002/0045442 A1 | 4/2002 | Silen et al. |
| 7,097,089 | B2 | 8/2006 | Marczyk | 2002/0069595 A1 | 6/2002 | Knudson et al. |
| 7,111,769 | B2 | 9/2006 | Wales et al. | 2002/0084304 A1 | 7/2002 | Whitman |
| 7,114,642 | B2 | 10/2006 | Whitman | 2002/0111621 A1 | 8/2002 | Wallace et al. |
| 7,121,446 | B2 | 10/2006 | Arad et al. | 2002/0143346 A1 | 10/2002 | McGuckin, Jr. et al. |
| 7,128,253 | B2 | 10/2006 | Mastri et al. | 2002/0177843 A1 | 11/2002 | Anderson et al. |
| 7,128,254 | B2 | 10/2006 | Shelton, IV et al. | 2002/0188294 A1 | 12/2002 | Couture et al. |
| 7,140,527 | B2 | 11/2006 | Ehrenfels et al. | 2002/0190093 A1 | 12/2002 | Fenton, Jr. |
| 7,140,528 | B2 | 11/2006 | Shelton, IV | 2003/0009193 A1 | 1/2003 | Corsaro |
| 7,143,923 | B2 | 12/2006 | Shelton, IV et al. | 2003/0105476 A1 | 6/2003 | Sancoff et al. |
| 7,143,924 | B2 | 12/2006 | Scirica et al. | 2003/0132268 A1 | 7/2003 | Whitman |
| 7,143,925 | B2 | 12/2006 | Shelton, IV et al. | 2004/0004105 A1 | 1/2004 | Jankowski |
| 7,143,926 | B2 | 12/2006 | Shelton, IV et al. | 2004/0007608 A1 | 1/2004 | Ehrenfels et al. |
| 7,147,138 | B2 | 12/2006 | Shelton, IV | 2004/0050902 A1 | 3/2004 | Green et al. |
| 7,159,750 | B2 | 1/2007 | Racenet et al. | 2004/0093029 A1 | 5/2004 | Zubik et al. |
| 7,172,104 | B2 | 2/2007 | Scirica et al. | 2004/0094597 A1 | 5/2004 | Whitman |
| 7,188,758 | B2 | 3/2007 | Viola et al. | 2004/0108357 A1 | 6/2004 | Milliman |
| 7,207,471 | B2 | 4/2007 | Heinrich et al. | 2004/0149802 A1 | 8/2004 | Whitman |
| 7,213,736 | B2 | 5/2007 | Wales et al. | 2004/0173659 A1 | 9/2004 | Green |
| 7,225,963 | B2 | 6/2007 | Scirica | 2004/0199180 A1 | 10/2004 | Knodel et al. |
| 7,225,964 | B2 | 6/2007 | Mastri et al. | 2004/0199181 A1 | 10/2004 | Knodel et al. |
| 7,238,195 | B2 | 7/2007 | Viola | 2004/0232199 A1 | 11/2004 | Shelton, IV et al. |
| 7,246,734 | B2 | 7/2007 | Shelton, IV | 2004/0232200 A1 | 11/2004 | Shelton, IV et al. |
| 7,258,262 | B2 | 8/2007 | Mastri et al. | 2004/0232201 A1 | 11/2004 | Wenchell |
| 7,278,562 | B2 | 10/2007 | Mastri et al. | 2004/0243151 A1 | 12/2004 | Demmy |
| 7,278,563 | B1 | 10/2007 | Green | 2004/0267310 A1 | 12/2004 | Racenet |
| 7,287,682 | B1 | 10/2007 | Ezzat et al. | 2004/0267311 A1 | 12/2004 | Viola et al. |
| 7,293,685 | B2 | 11/2007 | Ehrenfels et al. | 2005/0006429 A1 | 1/2005 | Wales |
| 7,296,724 | B2 | 11/2007 | Green et al. | 2005/0006430 A1 | 1/2005 | Wales |
| 7,296,772 | B2 | 11/2007 | Wang | 2005/0006431 A1 | 1/2005 | Shelton, IV et al. |
| 7,300,444 | B1 | 11/2007 | Nielsen et al. | 2005/0006432 A1 | 1/2005 | Racenet |
| 7,303,108 | B2 | 12/2007 | Shelton, IV | 2005/0006433 A1 | 1/2005 | Milliman |
| 7,308,998 | B2 | 12/2007 | Mastri et al. | 2005/0006434 A1 | 1/2005 | Wales et al. |
| 7,328,828 | B2 | 2/2008 | Ortiz et al. | 2005/0023324 A1 | 2/2005 | Doll et al. |
| 7,328,829 | B2 | 2/2008 | Arad et al. | 2005/0023325 A1 | 2/2005 | Gresham |
| 7,354,447 | B2 | 4/2008 | Shelton, IV et al. | 2005/0067457 A1 | 3/2005 | Shelton |
| 7,357,287 | B2 | 4/2008 | Shelton, IV et al. | 2005/0067458 A1 | 3/2005 | Swayze et al. |
| 7,364,061 | B2 | 4/2008 | Swayze et al. | 2005/0067459 A1 | 3/2005 | Swayze et al. |

| | | | | | |
|---|---|---|---|---|---|
| 2005/0067460 A1 | 3/2005 | Milliman | 2007/0084898 A1 | 4/2007 | Scirica |
| 2005/0070925 A1 | 3/2005 | Shelton, IV et al. | 2007/0084899 A1 | 4/2007 | Taylor |
| 2005/0070958 A1 | 3/2005 | Swayze et al. | 2007/0102472 A1 | 5/2007 | Shelton, IV |
| 2005/0072827 A1 | 4/2005 | Mollenauer | 2007/0102473 A1 | 5/2007 | Shelton, IV |
| 2005/0082336 A1 | 4/2005 | Ivanko | 2007/0102474 A1 | 5/2007 | Shelton, IV |
| 2005/0103819 A1 | 5/2005 | Racenet | 2007/0102475 A1 | 5/2007 | Ortiz et al. |
| 2005/0119669 A1 | 6/2005 | Demmy | 2007/0102476 A1 | 5/2007 | Shelton, IV |
| 2005/0127131 A1 | 6/2005 | Mastri | 2007/0106317 A1 | 5/2007 | Shelton, IV |
| 2005/0145671 A1 | 7/2005 | Viola | 2007/0108252 A1 | 5/2007 | Racenet et al. |
| 2005/0159778 A1 | 7/2005 | Heinrich et al. | 2007/0114261 A1 | 5/2007 | Ortiz et al. |
| 2005/0165415 A1 | 7/2005 | Wales | 2007/0114262 A1 | 5/2007 | Mastri et al. |
| 2005/0173490 A1 | 8/2005 | Shelton, IV | 2007/0119900 A1 | 5/2007 | Ehrenfels et al. |
| 2005/0178813 A1 | 8/2005 | Swayze et al. | 2007/0119901 A1 | 5/2007 | Ehrenfels et al. |
| 2005/0184121 A1 | 8/2005 | Heinrich | 2007/0125826 A1 | 6/2007 | Shelton, IV |
| 2005/0184123 A1 | 8/2005 | Scirica et al. | 2007/0125827 A1 | 6/2007 | Viola |
| 2005/0184124 A1 | 8/2005 | Scirica et al. | 2007/0125828 A1 | 6/2007 | Rethy |
| 2005/0184125 A1 | 8/2005 | Marczyk | 2007/0145095 A1 | 6/2007 | Heinrich et al. |
| 2005/0184126 A1 | 8/2005 | Green et al. | 2007/0145096 A1 | 6/2007 | Viola et al. |
| 2005/0189397 A1 | 9/2005 | Jankowski | 2007/0152014 A1 | 7/2007 | Gillum et al. |
| 2005/0192628 A1 | 9/2005 | Viola | 2007/0158385 A1 | 7/2007 | Hueil et al. |
| 2005/0216055 A1 | 9/2005 | Scirica et al. | 2007/0170225 A1 | 7/2007 | Shelton, IV et al. |
| 2005/0230453 A1 | 10/2005 | Viola | 2007/0175947 A1 | 8/2007 | Ortiz et al. |
| 2005/0263562 A1 | 12/2005 | Shelton, IV et al. | 2007/0175948 A1 | 8/2007 | Scirica et al. |
| 2005/0279804 A1 | 12/2005 | Scirica et al. | 2007/0175949 A1 | 8/2007 | Shelton, IV et al. |
| 2006/0000867 A1 | 1/2006 | Shelton, IV et al. | 2007/0175950 A1 | 8/2007 | Shelton, IV et al. |
| 2006/0000868 A1 | 1/2006 | Shelton, IV et al. | 2007/0175951 A1 | 8/2007 | Shelton, IV et al. |
| 2006/0011699 A1 | 1/2006 | Olson et al. | 2007/0175952 A1 | 8/2007 | Shelton, IV et al. |
| 2006/0016853 A1 | 1/2006 | Racenet | 2007/0175953 A1 | 8/2007 | Shelton, IV et al. |
| 2006/0022014 A1 | 2/2006 | Shelton, IV et al. | 2007/0175954 A1 | 8/2007 | Viola |
| 2006/0022015 A1 | 2/2006 | Shelton, IV et al. | 2007/0175955 A1 | 8/2007 | Shelton, IV et al. |
| 2006/0025809 A1 | 2/2006 | Shelton, IV | 2007/0175956 A1 | 8/2007 | Swayze et al. |
| 2006/0043147 A1 | 3/2006 | Mastri et al. | 2007/0175957 A1 | 8/2007 | Shelton, IV et al. |
| 2006/0049229 A1 | 3/2006 | Milliman et al. | 2007/0175958 A1 | 8/2007 | Shelton, IV et al. |
| 2006/0049230 A1 | 3/2006 | Shelton, IV et al. | 2007/0175959 A1 | 8/2007 | Shelton, IV et al. |
| 2006/0060630 A1 | 3/2006 | Shelton, IV et al. | 2007/0175960 A1 | 8/2007 | Shelton, IV et al. |
| 2006/0081678 A1 | 4/2006 | Ehrenfels et al. | 2007/0175961 A1 | 8/2007 | Shelton, IV et al. |
| 2006/0097026 A1 | 5/2006 | Shelton, IV | 2007/0175962 A1 | 8/2007 | Shelton, IV et al. |
| 2006/0124688 A1 | 6/2006 | Racenet et al. | 2007/0175964 A1 | 8/2007 | Shelton, IV et al. |
| 2006/0124689 A1 | 6/2006 | Arad et al. | 2007/0179528 A1 | 8/2007 | Soltz et al. |
| 2006/0138193 A1 | 6/2006 | Viola et al. | 2007/0187453 A1 | 8/2007 | Smith et al. |
| 2006/0138194 A1 | 6/2006 | Viola et al. | 2007/0187454 A1 | 8/2007 | Scirica |
| 2006/0151567 A1 | 7/2006 | Roy | 2007/0187455 A1 | 8/2007 | Demmy et al. |
| 2006/0151568 A1 | 7/2006 | Weller et al. | 2007/0194079 A1 | 8/2007 | Hueil et al. |
| 2006/0151569 A1 | 7/2006 | Ehrenfels et al. | 2007/0194080 A1 | 8/2007 | Swayze et al. |
| 2006/0163312 A1* | 7/2006 | Viola et al. ............... 227/175.1 | 2007/0194081 A1 | 8/2007 | Hueil et al. |
| 2006/0175375 A1 | 8/2006 | Shelton, IV et al. | 2007/0194082 A1 | 8/2007 | Morgan et al. |
| 2006/0180634 A1 | 8/2006 | Shelton, IV et al. | 2007/0221700 A1 | 9/2007 | Ortiz et al. |
| 2006/0201990 A1 | 9/2006 | Mastri et al. | 2007/0221701 A1 | 9/2007 | Ortiz et al. |
| 2006/0201991 A1 | 9/2006 | Mastri et al. | 2007/0278277 A1 | 12/2007 | Wixey et al. |
| 2006/0226195 A1 | 10/2006 | Scirica et al. | 2007/0295780 A1 | 12/2007 | Shelton et al. |
| 2006/0226196 A1 | 10/2006 | Hueil et al. | 2008/0029570 A1 | 2/2008 | Shelton et al. |
| 2006/0255090 A1 | 11/2006 | Milliman et al. | 2008/0029571 A1 | 2/2008 | Shelton et al. |
| 2006/0278680 A1 | 12/2006 | Viola et al. | 2008/0029572 A1 | 2/2008 | Shelton et al. |
| 2006/0278681 A1 | 12/2006 | Viola et al. | 2008/0029573 A1 | 2/2008 | Shelton et al. |
| 2006/0289600 A1 | 12/2006 | Wales et al. | 2008/0029574 A1 | 2/2008 | Shelton et al. |
| 2006/0289602 A1 | 12/2006 | Wales et al. | 2008/0029575 A1 | 2/2008 | Shelton et al. |
| 2007/0023477 A1 | 2/2007 | Whitman et al. | 2008/0029576 A1 | 2/2008 | Shelton et al. |
| 2007/0027469 A1 | 2/2007 | Smith et al. | 2008/0029577 A1 | 2/2008 | Shelton et al. |
| 2007/0034669 A1 | 2/2007 | de la Torre et al. | 2008/0048002 A1 | 2/2008 | Smith et al. |
| 2007/0034670 A1 | 2/2007 | Racenet et al. | 2008/0078800 A1 | 4/2008 | Hess et al. |
| 2007/0045379 A1 | 3/2007 | Shelton, IV | 2008/0078801 A1 | 4/2008 | Shelton et al. |
| 2007/0045380 A1 | 3/2007 | Mastri et al. | 2008/0078802 A1 | 4/2008 | Hess et al. |
| 2007/0068989 A1 | 3/2007 | Shelton, IV | 2008/0078803 A1 | 4/2008 | Shelton et al. |
| 2007/0068990 A1 | 3/2007 | Shelton, IV et al. | 2008/0078804 A1 | 4/2008 | Shelton et al. |
| 2007/0073340 A1 | 3/2007 | Shelton, IV et al. | 2008/0078805 A1 | 4/2008 | Omaits et al. |
| 2007/0073341 A1 | 3/2007 | Smith et al. | 2008/0078806 A1 | 4/2008 | Omaits et al. |
| 2007/0075114 A1 | 4/2007 | Shelton, IV et al. | 2008/0078807 A1 | 4/2008 | Hess et al. |
| 2007/0075115 A1 | 4/2007 | Olson et al. | 2008/0078808 A1 | 4/2008 | Hess et al. |
| 2007/0075116 A1 | 4/2007 | Whitman | 2008/0110958 A1 | 5/2008 | McKenna et al. |
| 2007/0083233 A1 | 4/2007 | Ortiz et al. | 2008/0110961 A1 | 5/2008 | Voegele et al. |
| 2007/0083234 A1 | 4/2007 | Shelton, IV et al. | 2008/0125812 A1 | 5/2008 | Zubik et al. |
| 2007/0084896 A1 | 4/2007 | Doll et al. | 2008/0149685 A1 | 6/2008 | Smith |
| 2007/0084897 A1 | 4/2007 | Shelton, IV et al. | 2008/0164296 A1 | 7/2008 | Shelton et al. |

| | | |
|---|---|---|
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 A | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 5/1975 |
| SU | 728848 | 5/1977 |
| SU | 659146 | 4/1979 |
| SU | 980703 | 12/1982 |
| SU | 990220 | 1/1983 |
| WO | WO 89/10094 | 11/1989 |
| WO | WO 9210976 | 7/1992 |
| WO | 9308754 | 5/1993 |
| WO | WO 8302247 | 7/1993 |
| WO | 9314706 | 8/1993 |

* cited by examiner

TISSUE STOP FOR SURGICAL INSTRUMENT

BACKGROUND

1. Technical field

The present disclosure relates generally to surgical instruments and, more specifically, to surgical instruments for surgically joining tissue.

2. Background of Related Art

Surgical stapling instruments used for applying parallel rows of staples through compressed living tissue are well known in the art. These surgical instruments are commonly employed for closing tissue or organs prior to transaction or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge and anvil assemblies, and a firing mechanism for ejecting the surgical staples from the cartridge assembly.

In use, a surgeon generally initially approximates the anvil and cartridge members. Next, the surgeon can fire the instrument to place staples in tissue. Additionally, the surgeon may use the same instrument or a separate instrument to cut the tissue adjacent or between the row(s) of staples. Alternatively, the surgical stapling instrument can sequentially eject the staples while the anvil and cartridge are approximated.

SUMMARY

The present disclosure relates to a surgical instrument for surgically joining tissue. The surgical instrument includes a handle assembly, an elongated portion, an end effector, and a stop member. The elongated portion extends distally from the handle assembly. The end effector is disposed adjacent a distal portion of the elongated portion and includes a first jaw member and a second jaw member. At least one jaw member is movable with respect to the other jaw member between spaced and approximated positions. The stop member is disposed adjacent a distal portion of the first jaw member and is pivotable with respect to the first jaw member between a first position, a significant portion of the stop member being positioned external to the first jaw member and a second position capturing the tissue between the first and second jaw member.

In various embodiments, the cartridge is curved with respect to the longitudinal axis.

The surgical instrument may further include a biasing member disposed in mechanical cooperation with the stop member, wherein the biasing member biases stop member towards its first position.

In certain embodiments, the stop member includes a base and a stopping portion, the base being operatively connected to the stopping portion. In some embodiments, the stopping portion is pivotally connected to the base. Alternatively, the stop member may be pivotally coupled to the first jaw member.

The first jaw member may include a knife channel. The stop member may further include a first leg and a second leg positioned on opposite sides of the knife channel.

The surgical instrument may additionally include first and second slots disposed on the first jaw member. Each of the first and second slots are adapted to receive at least a portion of one of the first and second legs therein. In some embodiments, each of the first and second legs is configured to move at least partially through the first or second slot when the stop member moves towards its second position.

In addition, the present disclosure relates to a tool assembly for use with a surgical instrument. Generally, this tool assembly includes an end effector and a stop member. The end effector has a first jaw member and a second jaw member. At least one jaw member being movable with respect to the other jaw member between spaced and approximated positions. The stop member is disposed adjacent a distal portion of the first jaw member and is pivotable with respect to the first jaw member between a first position wherein at least a portion of the stop member is positioned external to the first jaw member, and a second position capturing the tissue between the first jaw member and the second jaw member, wherein at least a portion of the stop member is positioned at least partially below a tissue-contacting surface of the first jaw member, wherein the relative movement of the jaw members toward the approximated position causes at least a portion of the stop member to move toward the first jaw member.

In some embodiments, the end effector includes a longitudinally curvilinear shape. Further, in certain embodiments, the stop member is biased toward the first position. The first jaw member may include at least one slot formed therein. This slot is configured to receive at least a portion of the stop member.

The present disclosure also relates to a stop member configured for use with a surgical instrument. The stop member includes a base portion configured to mechanically engage a jaw member of a surgical instrument, and a stopping portion. The stopping portion is pivotably engaged with the base portion and is movable between a first position and a second position. In the first position, the stopping portion is configured to facilitate tissue being moved proximally with respect to the stopping portion. In the second position, the stopping portion is configured to inhibit tissue from translating distally past the stopping portion.

BRIEF DESCRIPTION OF FIGURES

Various embodiments of the presently disclosed surgical instrument are disclosed herein with reference to the drawings, wherein.

DETAILED DESCRIPTION

Embodiments of the presently disclosed surgical instrument are described in detail with reference to the drawings, wherein like reference numerals designate similar or identical elements in each of the several views. In the drawings and the description that follows, the term "proximal" refers to the end of the surgical instrument that is closest to the operator, whereas the term "distal" refers to the end of the surgical instrument that is farthest from the operator. As appreciated by one skilled in the art, the depicted surgical instrument fires staples, but it may be adapted to fire any other suitable fastener such as clips and two-part fasteners. Additionally, the disclosed stop member may be used with an electrosurgical forceps. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

Figure 1:
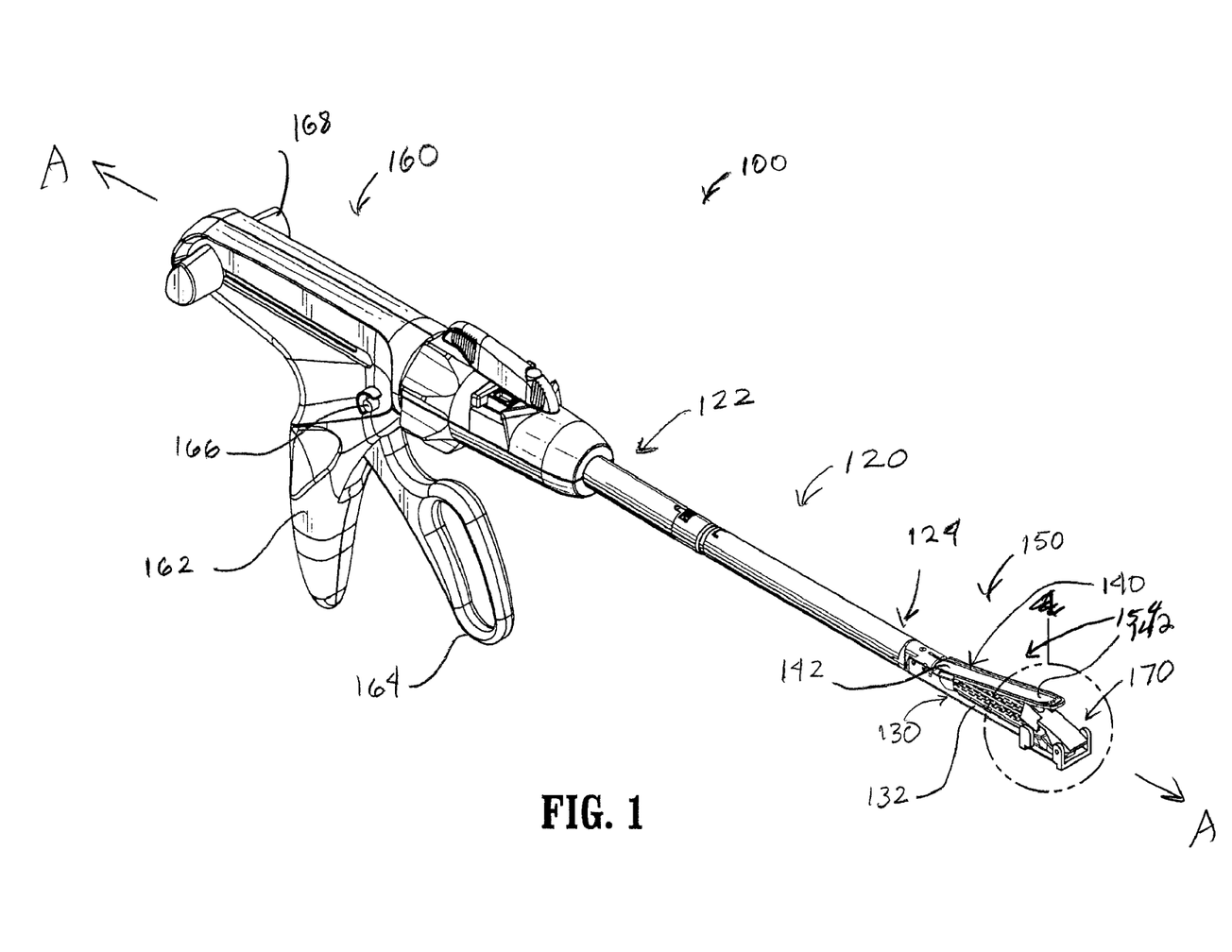
FIG. 1 is a perspective view of an embodiment of the surgical instrument of the present disclosure.
Figure 2:
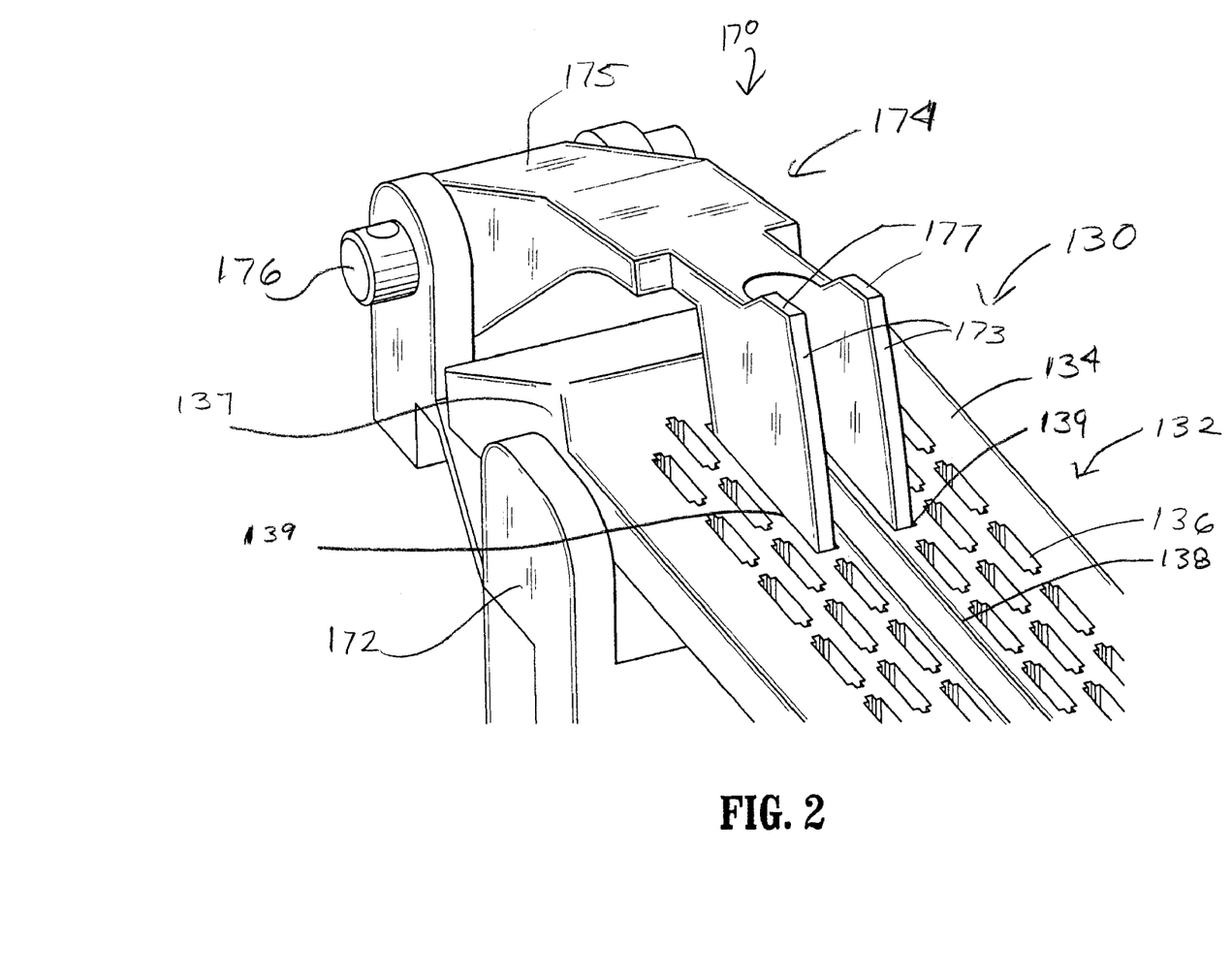
FIGS. 2-4 are perspective views of a portion of the surgical instrument of FIG. 1, showing a stop member in a first position.
Figure 3:
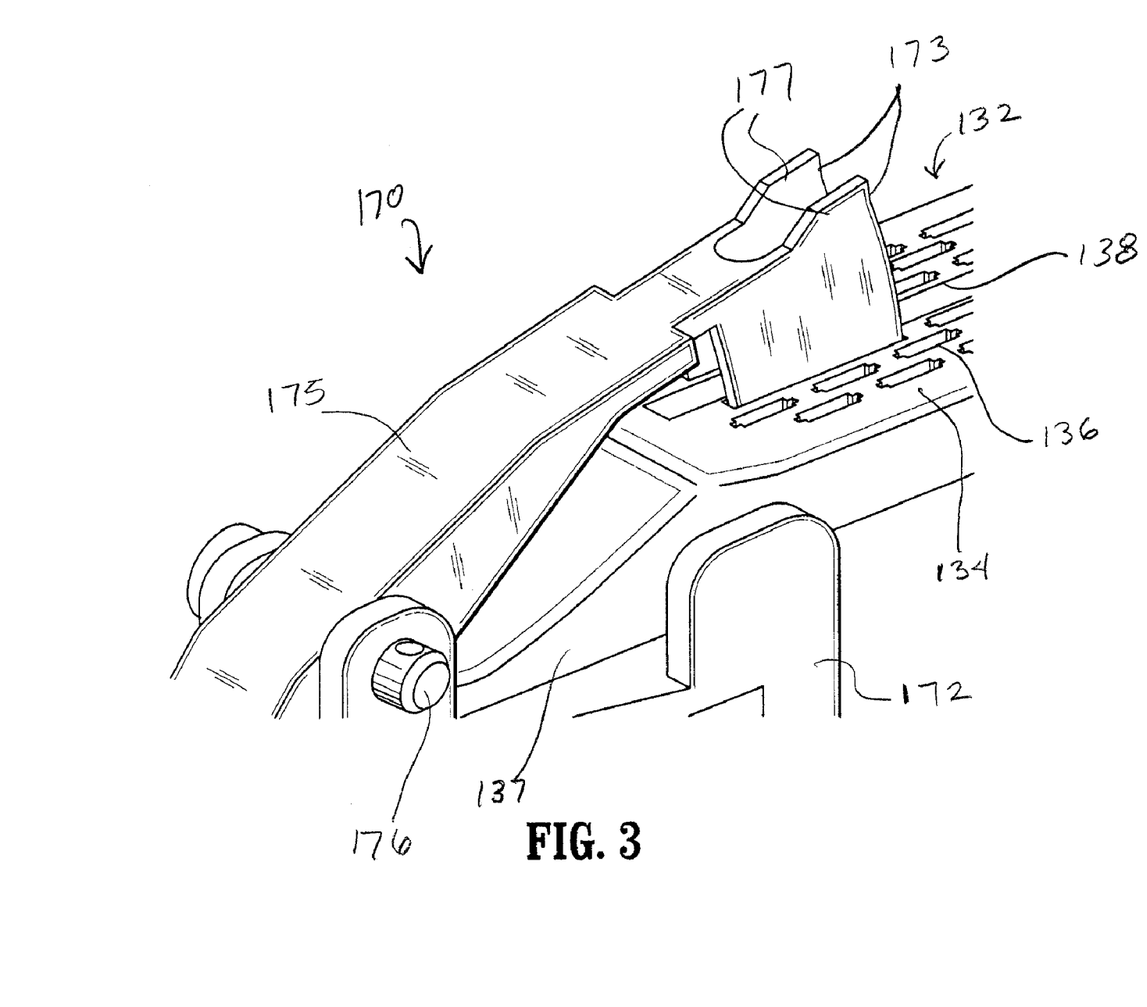

With reference to FIG. 1, reference numeral 100 designates an embodiment of the presently disclosed surgical instrument. In the interest of brevity, the present disclosure focuses on an end effector and a stop member of surgical instrument 100. U.S. Patent Applications Publication Nos. 2008/0105730, filed on Nov. 28, 2007; 2008/0110960, flied on Jan. 8, 2008; 2008/0142565, filed on Jan. 24, 2008; 2008/0041916, filed on Oct. 15, 2007 and U.S. Provisional Patent Application Ser. No. 61/050273, filed on May 5, 2008 and Ser. No. 11/786,198, filed on Apr. 10, 2007 describe in detail the structure and operation of other surgical fastening assemblies. The entire contents of these prior applications are incorporated herein by reference. Any of the surgical fastening assemblies disclosed in the cited patent applications may include the presently disclosed stop member.

Surgical instrument 100 is configured to clamp, fasten, and/or cut tissue. In general, surgical instrument 100 includes a handle assembly 160, an elongate portion 120 extending distally from handle assembly 160 and defining a longitudinal axis "A-A," and a tool assembly 150 adapted to clamp and fasten tissue. Elongate portion 120 has a proximal portion 122 and a distal portion 124 and operatively couples handle assembly 160 with tool assembly 150. Tool assembly 150 includes end effector 154 and stop member 170. End effector 154, which is disposed adjacent distal portion 124 of elongated portion 120, includes a first jaw member 130 and a second jaw member 140. At least one of the jaw members 130, 140 is adapted to move relative to the other jaw member (130 or 140) between spaced and approximated positions. In the illustrated embodiment, first jaw member 130 contains a cartridge assembly 132, while second jaw member 140 includes an anvil assembly 142. As discussed below, anvil assembly 142 moves with respect to cartridge assembly 132 between spaced and approximated positions upon actuation of handle assembly 160, for example. However, it is also envisioned that other methods of approximating the jaw members are also usable, including sliding a clamp bar 168.

Handle assembly 160 includes a stationary handle 162 and a movable handle 164. Movable handle 164 is adapted to move pivotally toward or away from stationary handle 162. Further, movable handle 164 is operatively connected to anvil assembly 140 through a mechanism adapted to convert at least a partial actuation of movable handle 164 into a pivoting motion of at least one of cartridge assembly 132 and anvil assembly 142 between spaced and approximated positions. As recognized by one skilled in the art, any conventional actuation mechanism may be employed to operatively couple movable handle 164 to tool assembly 150.

With reference to FIGS. 2-5, cartridge assembly 132 has a tissue-contacting surface 134 and a plurality of fastener retaining slots 136. Tissue-contacting surface 134 generally faces anvil assembly 142 (see FIG. 1) and, during operation, engages tissue when the anvil assembly 142 is approximated with cartridge assembly 132. Fastener retaining slots 136 are arranged in rows along tissue contacting surface 134. Each fastener retaining slot 136 is adapted to hold a fastener (not shown) until a user actuates handle assembly 160 (see FIG. 1), for example. When movable handle 164 is pivoted toward stationary handle 162, the fasteners are ejected from fastener retaining slots 134 and move toward anvil assembly 142.

In addition to fastener retaining slots 134, cartridge assembly 132 has a knife channel 138 adapted to slidably receive a knife (not shown) or any other suitable cutting tool. Knife channel 138 is disposed between rows of fastener retaining slots 136 and extends along tissue-contacting surface 134. In operation, a knife (not shown) slides through knife channel 138 when movable handle 164 pivots toward stationary handle 162. Alternatively, other mechanisms can be used to drive the knife through knife channel 138. In addition to knife channel 138, cartridge assembly 132 has a pair of slots 139 formed on tissue-contacting surface 134. Each slot 139 provides access to an inner portion of cartridge assembly 132 and is configured to receive portions of stop member 170.

In disclosed embodiments, handle assembly 160 contains an actuation mechanism for deploying the fasteners from fastener retaining slots 136 and advancing a knife along knife channel 138. This actuation mechanism includes a firing rod operatively connected to movable handle 164. In operation, pivoting movable handle 164 toward stationary handle 162 causes firing rod to advance distally. Firing rod is in turn operatively coupled to an axial drive assembly at least partially positioned within tool assembly 150. Axial drive assembly is configured to move distally in response to a distal translation of firing rod. The distal translation of axial drive assembly causes second jaw member 140 to pivot toward first jaw member 130. In addition, the axial drive assembly pushes an actuation sled disposed within first jaw member 130 in a distal direction, while the actuation sled translates distally through end effector 154. As the actuation sled advances distally through first jaw member 130, this actuation sled urges the fasteners out of the fastener retaining slots 136. In one embodiment, axial drive assembly includes a blade mounted on a distal portion thereof. In operation, this knife moves through knife channel 138 when axial drive assembly moves distally through end effector 154.

Figures 4, 5:
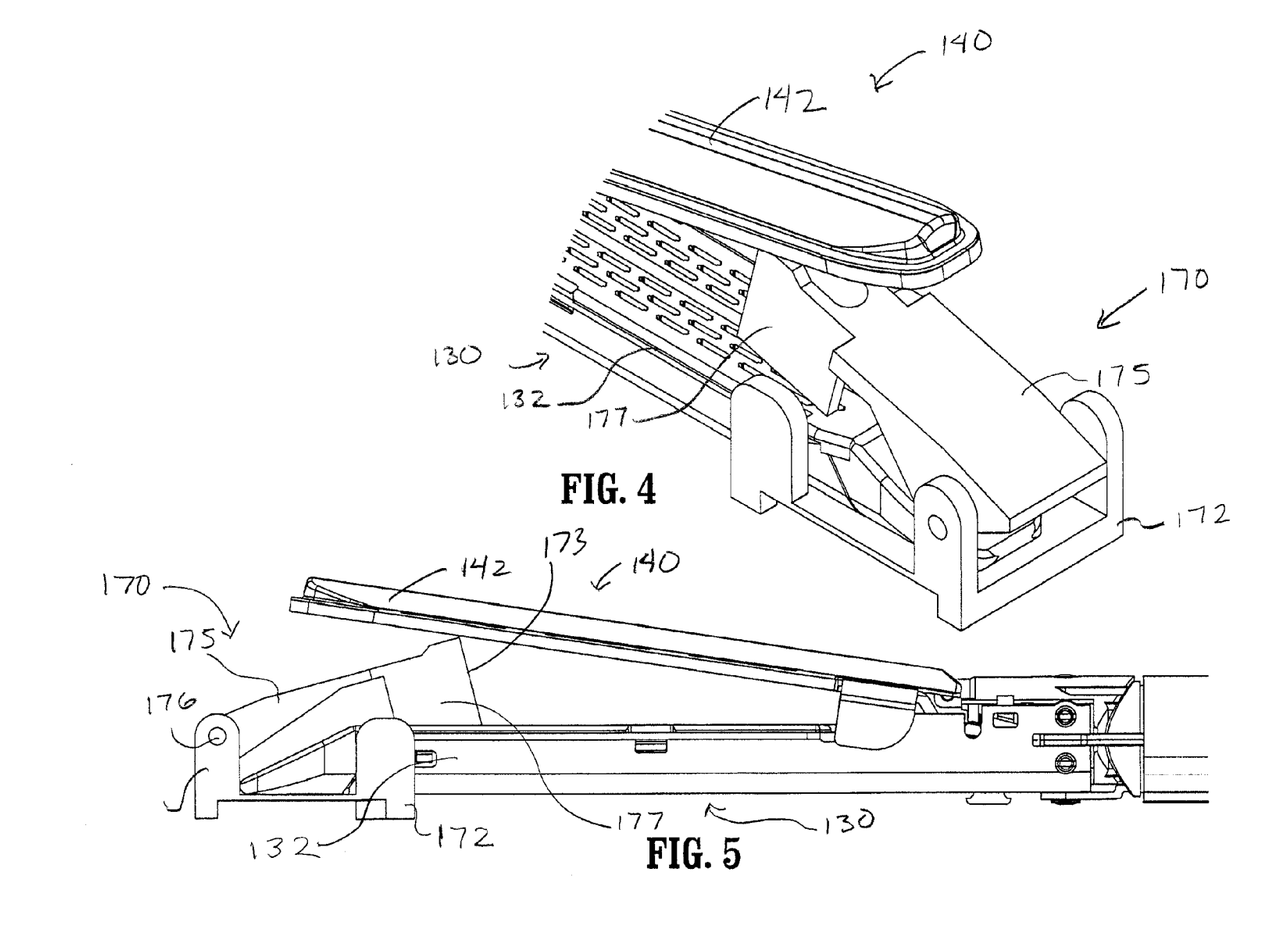
FIGS. 5-7 are side views of an end effector of the surgical instrument of FIG. 1, shown at different stages of operation.
Figure 7:
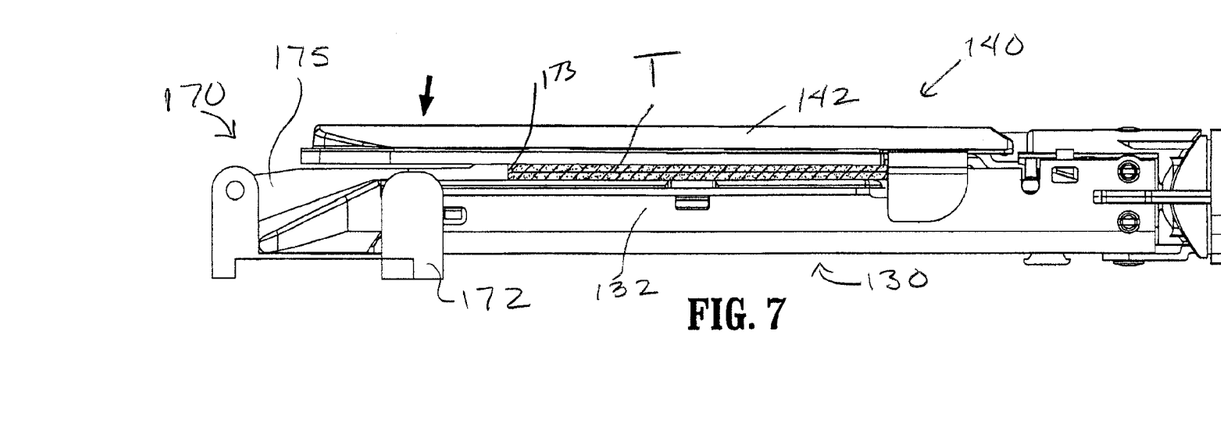

Stop member 170 is disposed adjacent a distal portion 137 of first jaw member 130 (which is shown as cartridge assembly 132, but may also be anvil assembly 142). The stop member 170 is pivotable with respect to the first jaw member 130 between a first position, as illustrated in FIG. 5, and a second position, as depicted in FIG. 7. In the first position, at least a portion of stop member 170 is located external to the first jaw member 130, whereas, in the second position, at least a portion of stop member 170 is positioned at least partially below tissue-contacting surface 134 of first jaw member 130. In various embodiments, a significant portion of stop member 170 is disposed external to the first jaw member 130 when stop member 170 is located in the first position. It is envisioned that the term "significant" means that at least half of each leg 177 of stop portion 170 is disposed external to the first jaw member 130 when stop member 170 is located in the first position. Additionally, as used herein, "significant" may mean that more than one-third of stop member 170 is disposed external to the first jaw member 130 when stop member 170 is located in the first position Stop member 170 includes a base 172 adapted to engage an outer surface of distal portion 137 of first jaw member 130 and a stopping portion 174 adapted to engage tissue. A pivot pin 176, or any other suitable apparatus, pivotally connects stopping portion 174 to base 172. Consequently, stopping portion 174 is configured to pivot away and toward tissue-contacting surface 134. In one embodiment, stop member 170 includes a biasing member (e.g., a spring) for biasing stopping portion 174 away from first jaw member 130.

Stopping portion 174 contains a body 175 and at least one leg 177 extending proximally from body 175. In the embodiment depicted in FIG. 2, stopping portion 174 has two legs 177 extending proximally from body 175. Stopping portion 174 may nonetheless include more or fewer legs 177. The two legs 177 shown in FIG. 2 define a space therebetween adapted to receive a knife. Each leg 177 is dimensioned to be received within a slot 139 and includes a proximal surface 173. When stop member 170 is located in the first position, each proximal surface 173 defines an oblique angle relative to tissue-contacting surface 134, as seen in FIG. 5. Conversely, when stop member 170 is located in the second position (see FIG. 7), each proximal surface 173 defines an angle substantially perpendicular to tissue-contacting surface 134. Irrespective of the position of stop member 170, legs 177 are shown positioned on opposite sides of knife channel 138. Slots 139, which are dimensioned to receive legs 177, are accordingly located on opposite sides of knife channel 138 as well.

Figure 6:
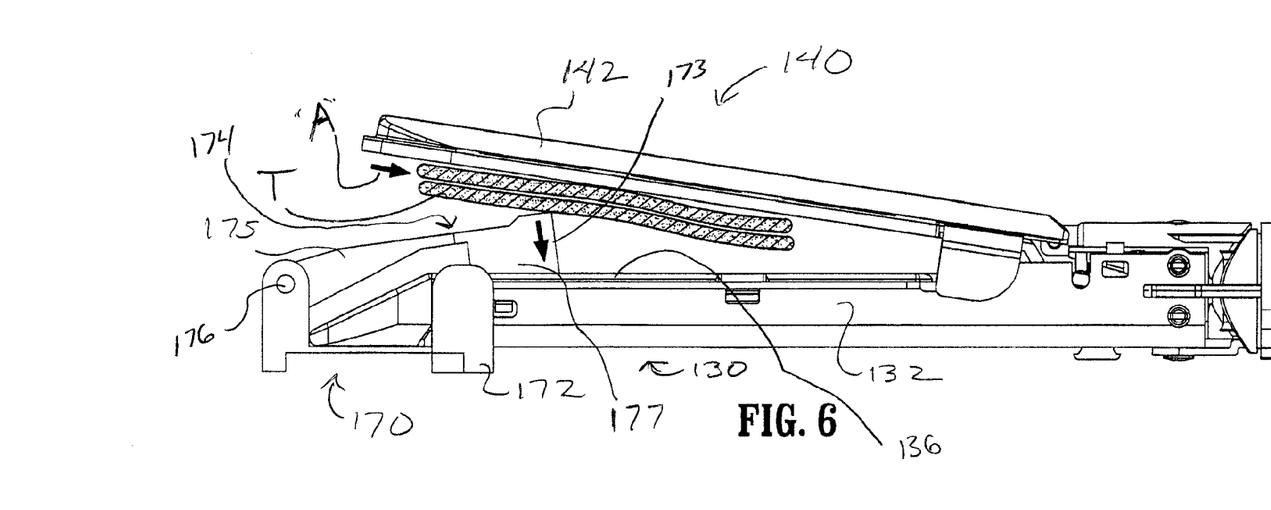
Figure 8:
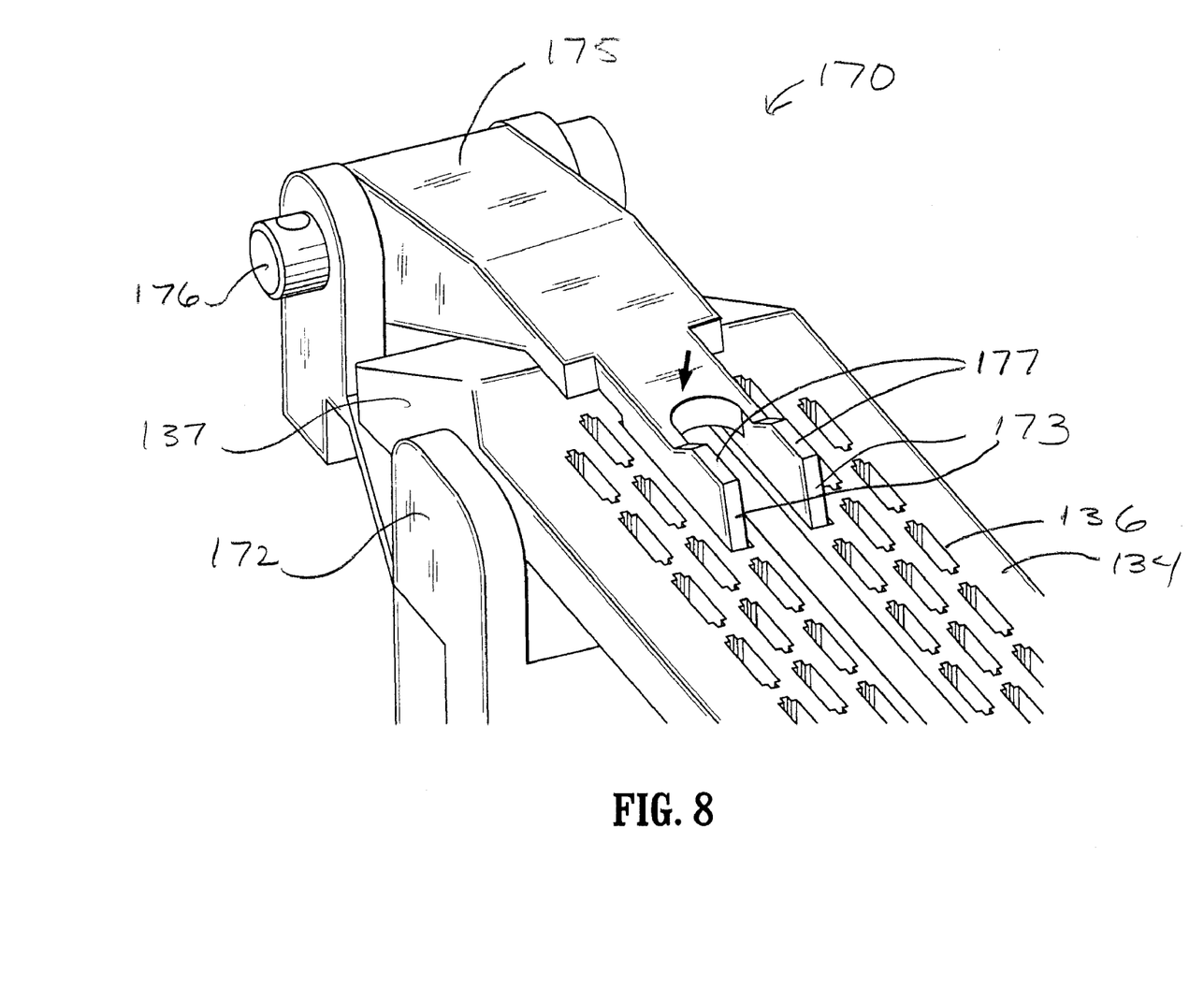
FIG. 8 is a perspective view of a portion of the surgical instrument of FIG. 1, showing a stop member adjacent its second position.

Referring to FIGS. 6-8, stop member 170 facilitates retention of tissue between first and second jaw members 130, 140 during the operation of surgical instrument 100. (See FIG. 1). That is, stop member 170 helps prevent tissue from migrating or translating distally past its intended placement between the jaw members. In use, a user initially positions surgical instrument 100 adjacent a target tissue. Particularly, the target tissue is placed between first and second jaw members 130, 140. The angle defined by body 175 relative to tissue-contacting surface 136 facilitates introduction of the target tissue "T" into tool assembly 150 in the general direction of arrow "A," as seen in FIG. 6. Once the user has placed at least a portion of the target tissue between first and second jaw members 130, 140, the user pulls movable handle 164 toward stationary handle 162 to approximate anvil assembly 152 toward cartridge assembly 132. While the user pulls movable handle 164, anvil assembly 152 moves closer to cartridge assembly 132 and the target tissue "T" is captured between tissue-contacting surface 134 of cartridge assembly 132. At the same time, anvil assembly 142 urges stopping portion 174 toward cartridge assembly 132. In response to the force exerted by the anvil assembly 142 on stopping portion 174, stopping portion 174 pivots about pivot pin 176 toward cartridge assembly 132, e.g., against the bias of biasing member (not shown). While stopping portion 174 moves closer to cartridge assembly 134, at least a portion of legs 177 move to an inner portion of cartridge assembly 132 through slots 139, as seen in FIG. 7. When stop member 170 is in the second position (as shown in FIG. 7), a portion of legs 177 is located within cartridge assembly 132; correspondingly, a portion of proximal surfaces 173 is located outside of cartridge assembly 132. As discussed above, proximal surfaces 173 define a substantially orthogonal angle relative to tissue-contacting surface 134 when stop member 170 is in the second position, thereby hindering the escape of tissue during clamping.

The present disclosure also contemplate stop member 170 being releasably attachable to end effector 150 via conventional mechanical means, e.g., bayonet coupling, latch, detent or snap-fit connection.

With reference to FIGS. 9-12, another embodiment of first jaw member 230 is envisioned. First jaw member 230 of this embodiment has a curved shape (i.e., with respect to longitudinal axis "A-A"). It is envisioned that curved jaw members may facilitate performing certain types of surgical procedures. For example, curved jaw members, as compared to straight jaw members (such as the jaw members illustrated in FIG. 1), may help facilitate access to lower pelvic regions, e.g., during lower anterior resection ("LAR") or other colorectal surgery.

First jaw member 230 includes an opening 239 (FIG. 10) adapted to receive both legs 277 of stop portion 270 instead of two slots 139 each capable of receiving a leg 177 of stop member 170. Stop member 270 is similar to stop member 170. However, stop member 270 has a stopping portion 274 directly connected to a distal portion 237 of first jaw member 230. Distal portion 237 contains a hole 235 (FIG. 10) adapted to receive a pivot pin 276. Pivot pin 276, or any other suitable apparatus, pivotally couples stop member 270 to first jaw member 230.

In general, first jaw member 230 includes a curved housing 231 and a curved cartridge assembly 232. Housing 231 has a curved channel 233 adapted to receive curved cartridge assembly 232. Curved cartridge assembly 232 contains a tissue-contacting surface 234 configured to engage tissue, rows of fastener retaining slots 236 extending along its curved profile, and a knife channel 238 adapted to slidably receive a knife (not shown). Knife channel 238 is disposed between the rows of fastener retaining slots 236.

As discussed above, actuating handle assembly 160 not only ejects the fasteners, but also drives a knife along knife channel 238 (e.g., via a single stroke or multiple strokes of movable handle 164). Knife channel 238 leads to an opening 239 formed on distal portion 237 of cartridge assembly 232. A recess 280 is positioned distally of opening 239 and includes an inclined wall 282 (see FIG. 11) defining an oblique angle relative to tissue-contacting surface 234 and is adapted to receive a portion of stop member 270 therein. In addition to inclined wall 282, recess 280 has a cavity 284 adapted to receive a portion of stop member 270.

Figure 9:
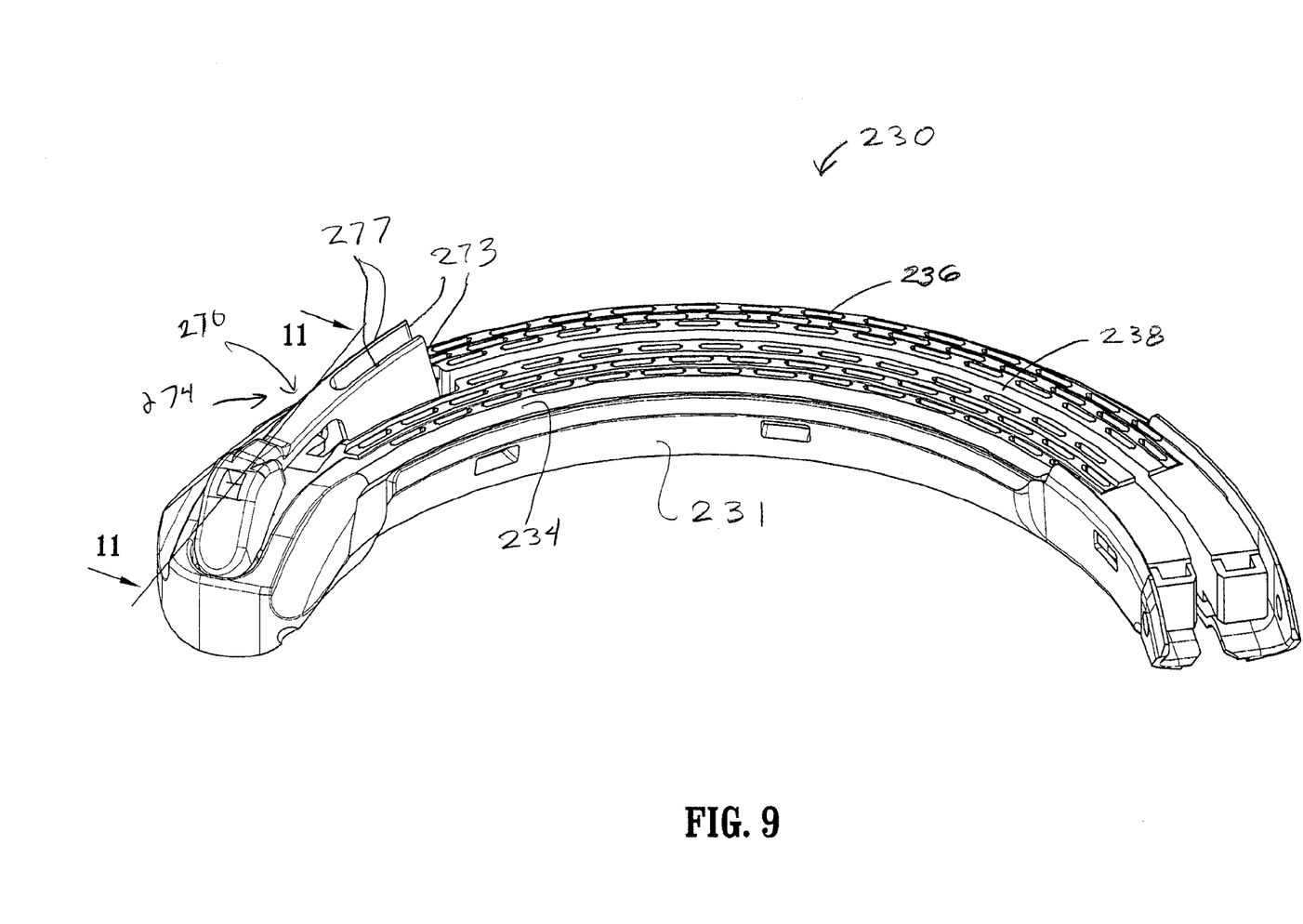
FIG. 9 is a perspective view of a curved jaw member according to another embodiment of the present disclosure, showing a stop member in a first position.
Figure 10:
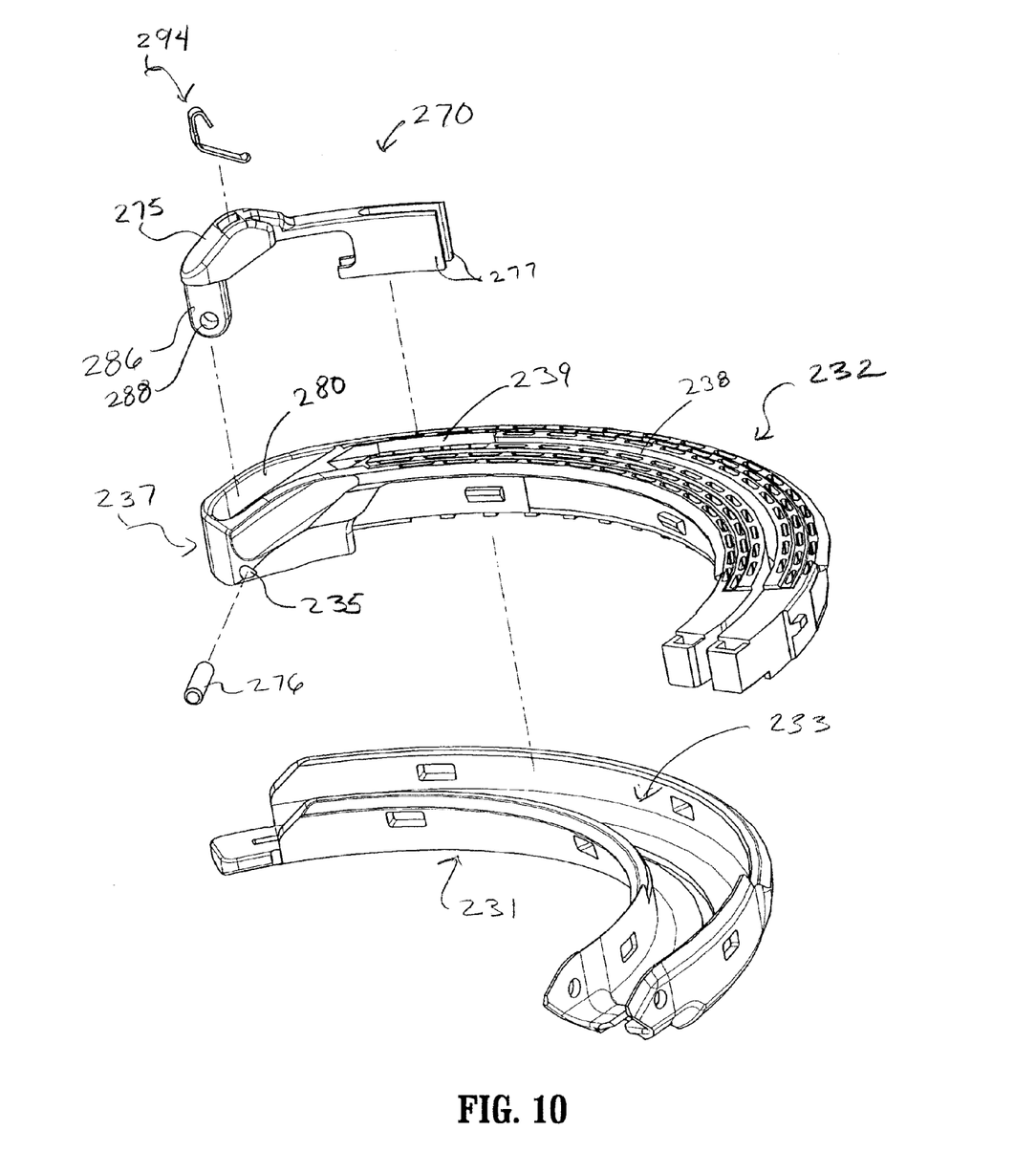
FIG. 10 is a perspective exploded view of the curved jaw member of FIG. 9.
Figure 12:
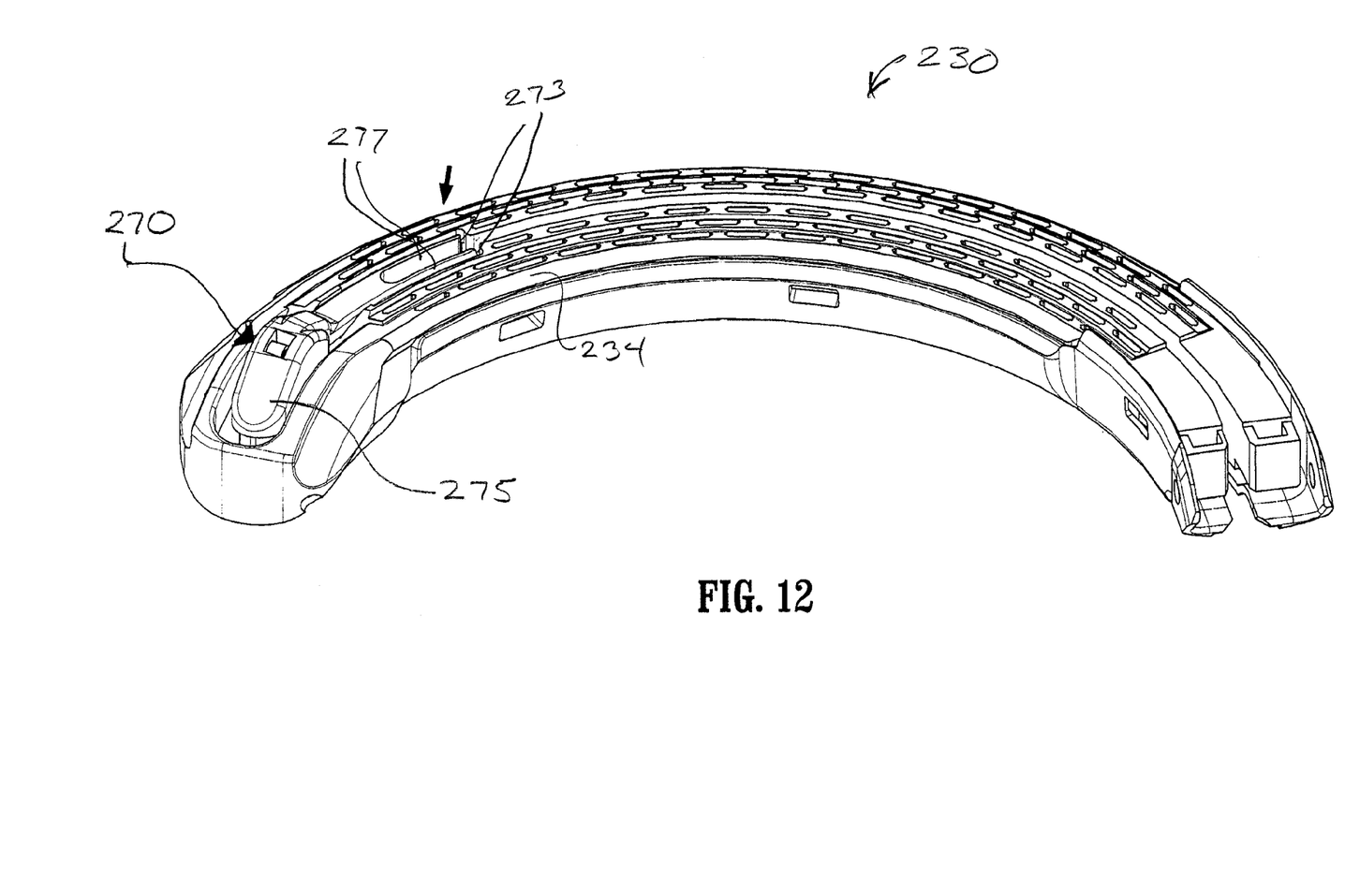
FIG. 12 is a perspective view of the curved jaw member of FIG. 9, showing the stop member in a second position.

Stop member 270 includes a body 275, a pair of legs extending proximally from body 275, and a pivoting protrusion 286 extending transversely from body 275. Legs 277 define a space therebetween dimensioned to receive a knife. Each leg 277 has a proximal surface 273 that defines an oblique angle relative to tissue-contacting surface 234 when stop portion 270 is in the first position, as shown in FIG. 9, and a substantially perpendicular angle relative to tissue-contacting surface 234 when stop portion 270 is in the second position, as illustrated in FIG. 12.

Body 275 defines an oblique angle with respect to the tissue-contacting surface 234. Pivoting protrusion 286 of stop member 270 is adapted to be received within cavity 284 and has a hole 288 configured to receive pivot pin 276. Pivot pin 276 extends through hole 235 of cartridge assembly 270 and hole 280 of pivoting protrusion 286 and allows stop member 270 to pivot from a first position where at least a portion of the stop member 270 is positioned external to first jaw member 230, as seen in FIG. 9, and a second position where at least a portion of stop member 270 is positioned at least partially below a tissue-contacting surface 234 of the first jaw member 230, as seen in FIG. 12.

Figure 11:
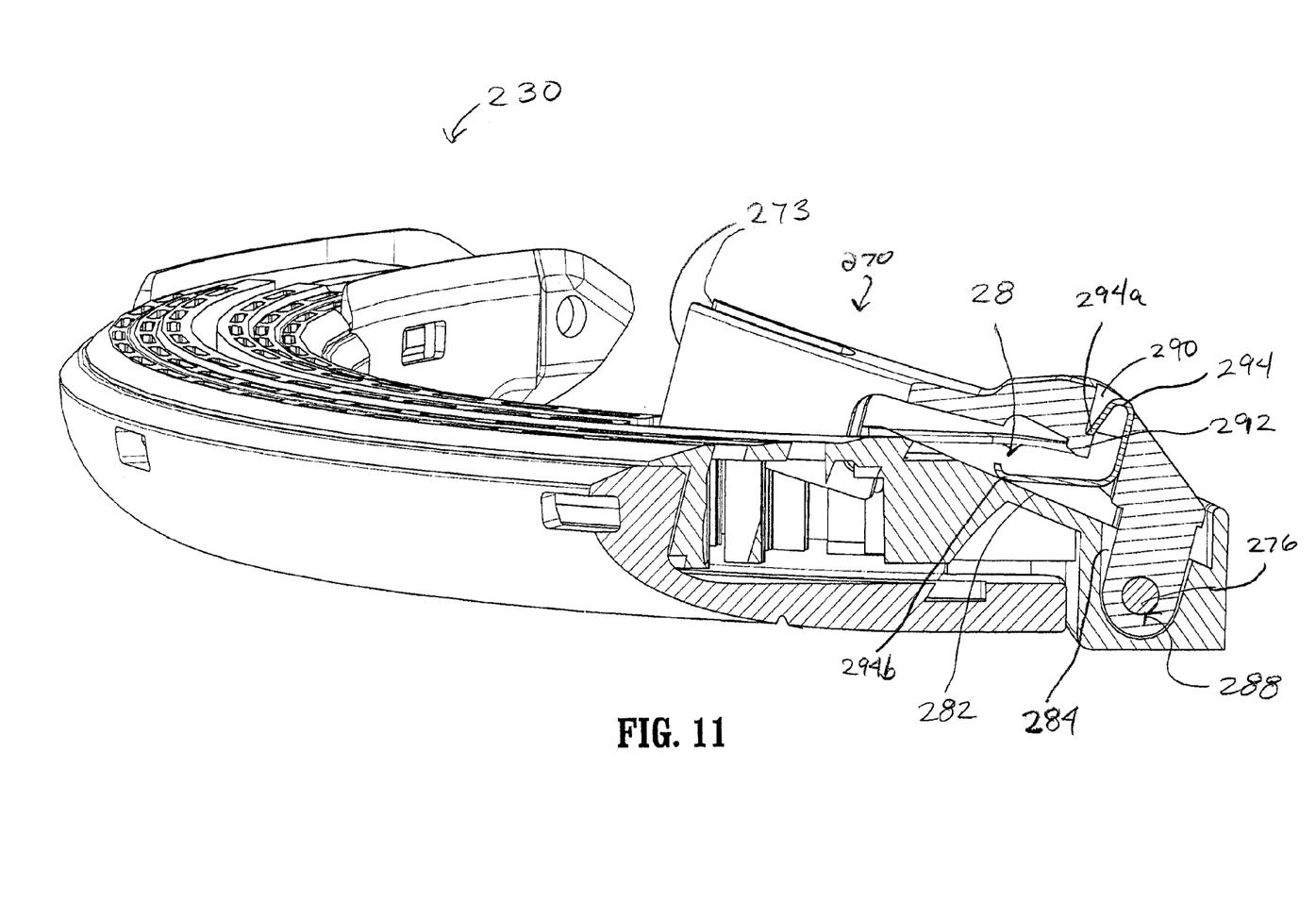
FIG. 11 is a perspective view of the curved jaw member of FIG. 9, showing the cross-section of a distal portion taken along section line 11-11 of FIG. 9.

As seen in FIG. 11, body 276 additionally contains a thru-hole 290 leading to inclined wall 282 and an abutment wall 292 protruding toward thru-hole 290. Abutment wall 292 is configured to hold a first end 294a of a biasing member 294, and inclined wall 282 is adapted to support a second end 294b of biasing member 294. Biasing member 294 biases stop member 270 towards its first position. In the embodiment depicted in FIGS. 10 and 11, biasing member 294 is a spring, but biasing member 294 can alternatively be any suitable apparatus or means capable of biasing stop member 270 away from first jaw member 230.

The operation of first jaw member 230 is substantially similar to the operation of first jaw member 130. First jaw member 230 works jointly with an anvil assembly to cut and/or fasten tissue. As a user actuates handle assembly 160, the jaw members approximate, which urges stop member 230 from the first position (see FIG. 9) to a second position (see FIG. 12). In the first position, the orientation of stop member 230 facilitates the introduction of tissue between first jaw member 230 and an anvil assembly. Further, stop member 230 inhibits tissue from distally escaping the tool assembly when stop member 230 is oriented in its second position. When the anvil assembly moves away from first jaw member 230, stop member 230, under the influence of biasing member 294, returns to its first position.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

What is claimed is:

1. A surgical instrument for surgically joining tissue, the surgical instrument comprising:
    a handle assembly;
    an elongated portion extending distally from the handle assembly and defining a longitudinal axis;
    an end effector disposed adjacent a distal portion of the elongated portion, the end effector including a first jaw member and a second jaw member, the first jaw member including a knife channel, at least one jaw member being movable with respect to the other jaw member between spaced and approximated positions; and
    a stop member disposed adjacent a distal portion of the first jaw member, the stop member being pivotable with respect to the first jaw member between a first position, a significant portion of the stop member being positioned external to the first jaw member, and a second position capturing the tissue between the first jaw member and second jaw member,
    wherein the stop member includes a first leg and a second leg, the first leg and the second leg being positioned on opposite sides of the knife channel.

2. The surgical instrument of claim 1, further comprising first and second slots disposed on the first jaw member, each of the first and second slots being adapted to receive at least a portion of one of the first and second legs therein.

3. The surgical instrument of claim 2, wherein each of the first and second legs is configured to move at least partially through the first or second slot when the stop member moves towards its second position.

4. The surgical instrument of claim 1, wherein the first jaw member comprises a surgical staple cartridge.

5. The surgical instrument of claim 4, wherein the staple cartridge is curved with respect to the longitudinal axis.

6. The surgical instrument of claim 1, further comprising a biasing member disposed in mechanical cooperation with the stop member, wherein the biasing member biases stop member towards its first position.

7. The surgical instrument of claim 1, wherein the stop member includes a base and a stopping portion, the base being operatively connected to the stopping portion.

8. The surgical instrument of claim 7, wherein the stopping portion is pivotally connected to the base.

* * * * *